US00PP24932P3

(12) United States Plant Patent

Scalzo et al.

(10) Patent No.: US PP24,932 P3
(45) Date of Patent: Sep. 30, 2014

(54) BLUEBERRY PLANT NAMED 'VELLUTO BLUE'

(50) Latin Name: *Vaccinium corymbosum*
Varietal Denomination: Velluto Blue

(75) Inventors: Jessica Scalzo, Havelock North (NZ); Narandra Patel, Hamilton (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 170 days.

(21) Appl. No.: 13/507,414

(22) Filed: Jun. 26, 2012

(65) Prior Publication Data

US 2013/0347149 P1 Dec. 26, 2013

(51) Int. Cl.
*A01H 5/00* (2006.01)

(52) U.S. Cl.
USPC ..... Plt./157

(58) Field of Classification Search
CPC ..... A01H 5/08; A01H 5/00
USPC ..... Plt./157
See application file for complete search history.

(56) References Cited

U.S. PATENT DOCUMENTS

| | | | |
|---|---|---|---|
| PP20,515 | P3 | 12/2009 | Patel |
| PP21,720 | P3 | 2/2011 | Patel |
| PP21,721 | P3 | 2/2011 | Patel |
| PP21,735 | P3 | 3/2011 | Patel |
| PP21,736 | P3 | 3/2011 | Patel |
| PP21,761 | P3 | 3/2011 | Patel |
| PP21,881 | P3 | 4/2011 | Patel |

*Primary Examiner* — June Hwu
(74) *Attorney, Agent, or Firm* — Lathrop & Gage LLP

(57) ABSTRACT

A new and distinct rabbiteye blueberry variety is described. The variety results from selection among a population of seedlings derived from the controlled crossing of the blueberry varieties 'Maru' (not patented) and 'Briteblue' (not patented). The fruit of this new variety has an attractive appearance characterised by outstanding fruit quality with a good bloom and little grittiness, and medium to late fruiting season. The new variety appears suitable for the medium to late fresh fruit market and has been named 'Velluto Blue'.

3 Drawing Sheets

Genus and species of plant claimed: *Vaccinium corymbosum.*

Variety denomination: 'VELLUTO BLUE'.

BACKGROUND OF THE INVENTION

The new variety was selected from among a population of seedlings derived from the deliberate crossing of the varieties named 'Maru' (not patented) as the seed parent and 'Briteblue' (not patented) as the pollen parent, located at Ruakura, Hamilton, New Zealand. F128 was identified as having potential as a new variety and was asexually propagated by cuttings. The plant was first asexually reproduced by personnel of The New Zealand Institute for Plant and Food Research Limited located at the research centre at Bisley Road, Ruakura, Hamilton, New Zealand. The resulting plants were subsequently found to be true to type demonstrating that the characteristics of the new variety are stable and transmitted without change through succeeding generations. Since the initial propagation in vitro propagation has also been carried out successfully. F128 was later given the denomination 'Velluto Blue'.

SUMMARY OF THE INVENTION

'Velluto Blue' is characterised by its attractive fruit with outstanding quality and flavour along with little grittiness and mid to late harvest season. 'Velluto Blue' is distinguished from a number of other varieties by the following characteristics:

The fruit of 'Velluto Blue' are larger than those of 'Centurion' (not patented) and 'Powderblue' (not patented) though of a similar average size to 'Centra Blue' (U.S. Plant Pat. No. 20,515).

The shape of 'Velluto Blue' fruit is oblate while those of 'Centra Blue' are oblong to round, 'Velluto Blue' was also observed to have a higher average Brix level than 'Centra Blue'.

The new variety was determined to be distinct from the parent varieties 'Maru' by its greater plant vigour, later fruit flowering, and higher yields, and 'Briteblue' by its later harvest period.

BRIEF DESCRIPTION OF THE DRAWINGS

The accompanying photographs show typical specimens of the plant, foliage and fruit of the new variety as depicted in colours as nearly true as is reasonably possible to make the same in a colour illustration of this character. Unless otherwise specified, the photographs depict mature (5 year old) plants or juvenile (<2 year old) plants grown at, Ruakura, Hamilton, New Zealand.

DETAILED DESCRIPTION OF THE VARIETY

Figure 1A:
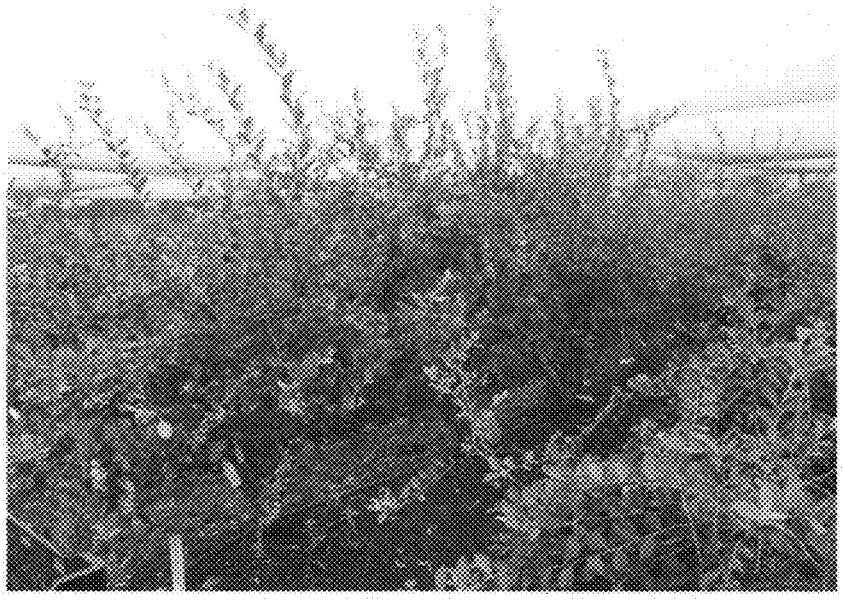
FIG. 1 shows 'Velluto Blue' plants a) mature, and b) juvenile.
Figure 1B:
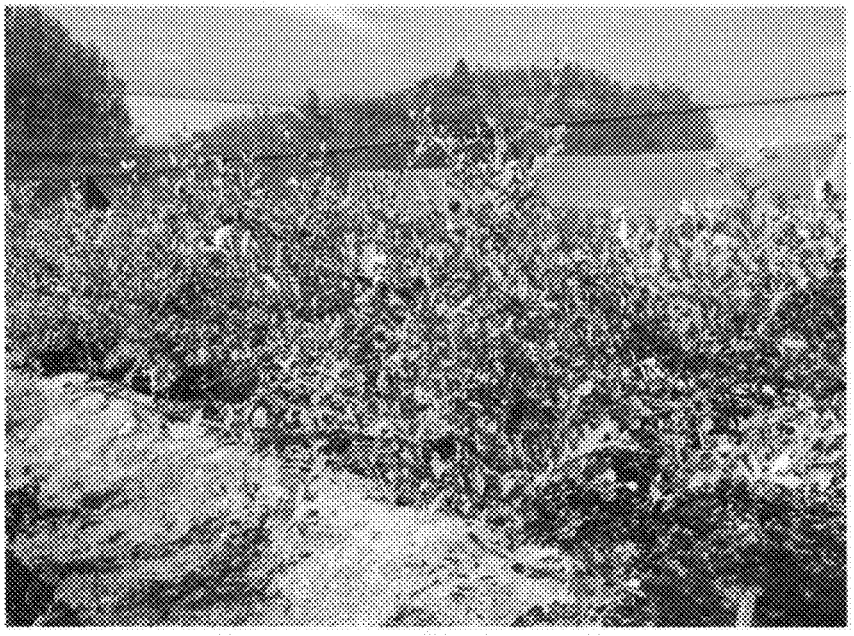
Figure 2A:
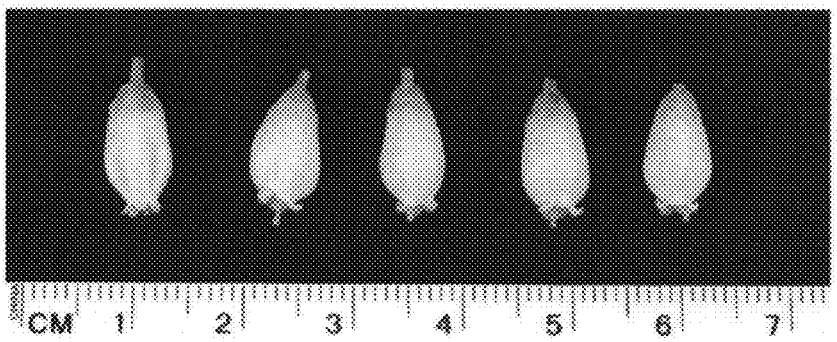
FIG. 2 shows 'Velluto Blue' flowers a) whole, b) longitudinal section, c) typical flowering branch.
Figure 2B:
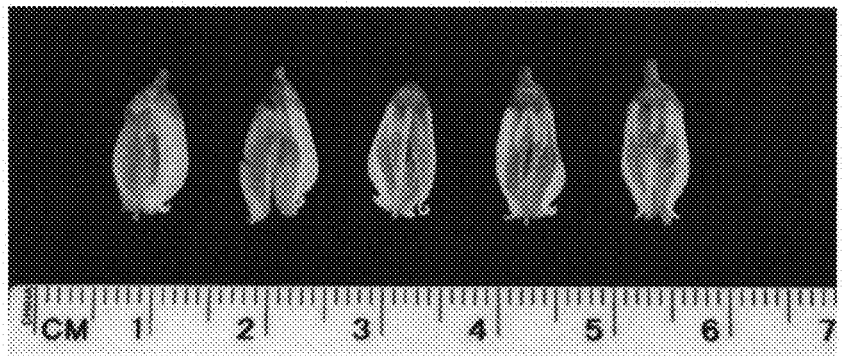
Figure 2C:
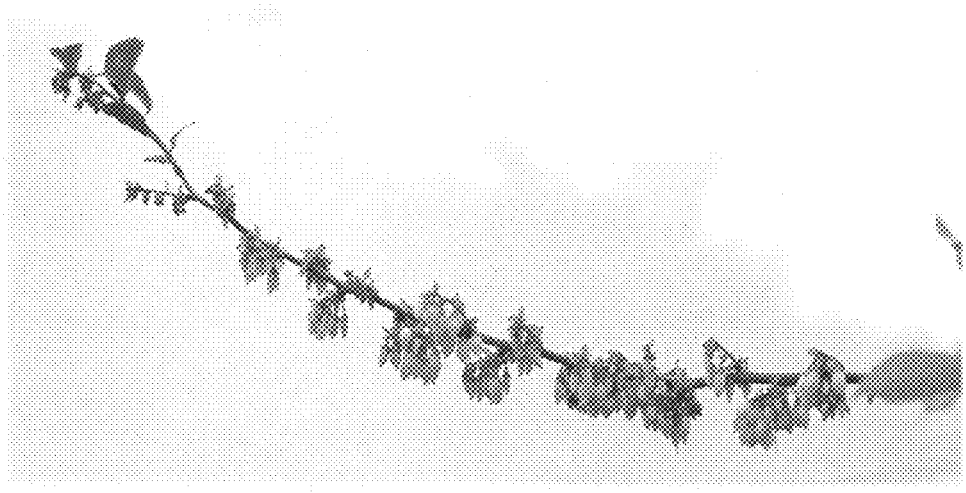
Figure 3:
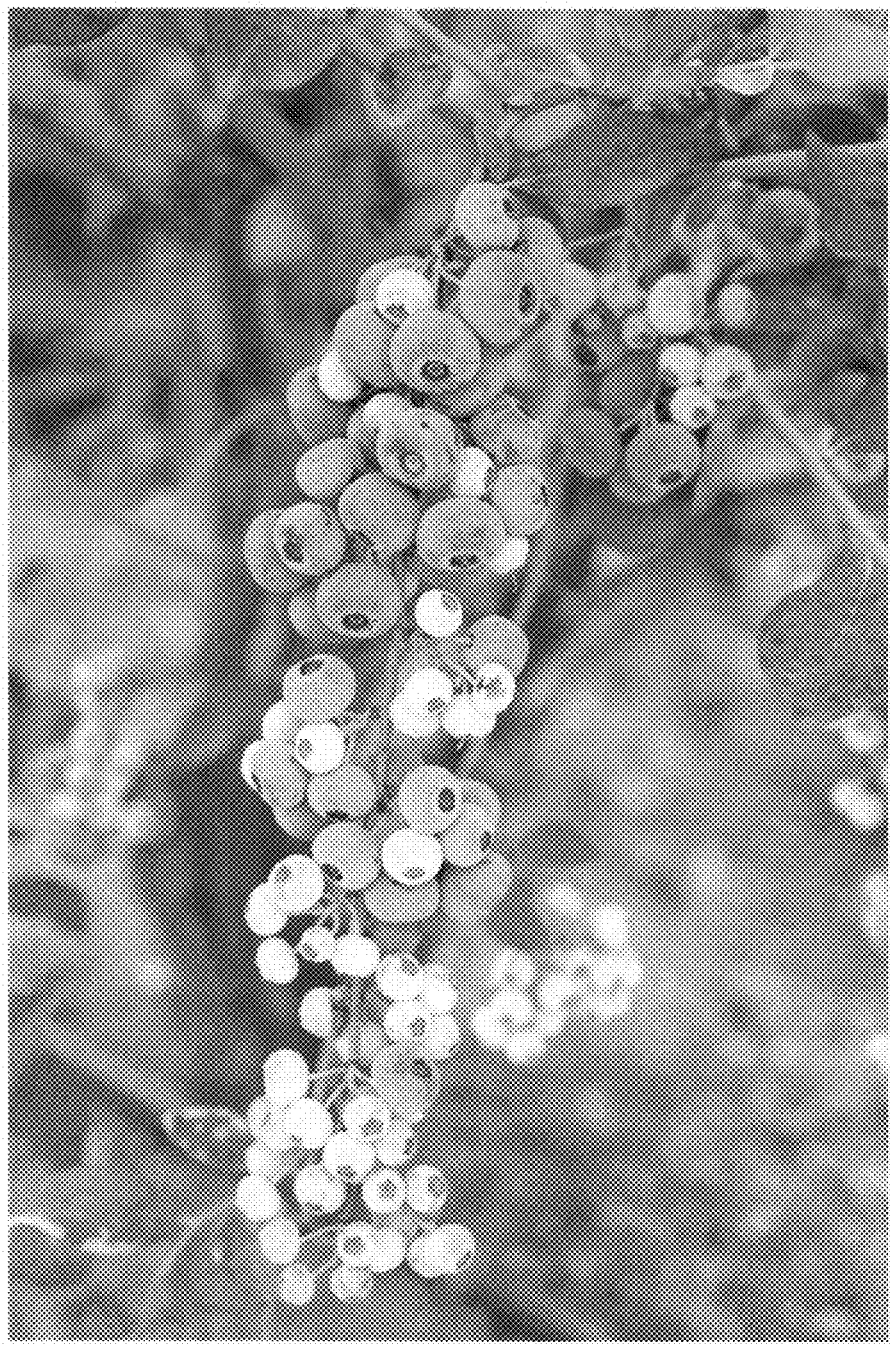
FIG. 3 shows fruit of 'Velluto Blue' on the plant.

The observations, unless otherwise specified, were made in the 2009-2010, 2010-11 and 2011-12 seasons on 5 year old plants grown at Ruakura, Hamilton, New Zealand. All dimensions in millimetres, weights in grams (unless otherwise stated). Colour terminology is in accordance with The Royal Horticultural Society Colour Charts (R.H.S.C.C.) 2001 edition.

Plant and Foliage

This hexaploid plant is generally semi-upright in growth habit, of medium to high vigour compared to 'Maru'. Plants have been observed to be taller in their development compared with other commercial varieties, such as, 'Maru' (not patented); plants 1 m to 1.5 m in height have been observed.

The surface texture of immature canes is smooth while the surface texture of mature canes is peeling; the bark of plant stem becomes peeling as the wood matures. The colour of immature canes is near R.H.S.C.C. Greyed-Green 195A. The colour of the bark of mature canes is near R.H.S.C.C. Greyed-Orange 174B.

The mature leaf is lanceolate in shape and typically averages 60-65 mm in length and approximately 35 mm in width. The margins generally have a minor serration, with moderate and uniform glossiness on the upper surface. The upper surface of the leaf is near R.H.S.C.C. Green 136A in colour. The petiole typically averages 3.3 mm in length.

Inflorescence

The average number of flower buds per branch is 14 with an observed range of 10-21.

Flowers are generally clustered and the typical flower averages 6.3 mm in diameter and 8.6 mm in height, with the opening of the flower averaging 3.6 mm across. The shape of the corolla is campanulate. The main colour of the petals on fully open mature flowers is near R.H.S.C.C. White 155C. The anthocyanin coloration of the flower bud is weak, with no anthocyanin coloration of the corolla tube observed. Ridges are present on the corolla tube. The stigma extends out of the corolla in some instances. The anther coloration is near R.H.S.C.C. Yellow-Orange 23A.

Fruit

The fruit are of large size compared to that typical of other Rabbiteye blueberry varieties, averaging approximately 2.4 g (observed range 2.1-2.9 g). Fruiting occurs on one year old shoots only; flowers do not occur on current season's shoots. The time of beginning of fruit ripening on one year old shoots is late, similar to that on 'Maru'.

Generally fruit is oblate in shape with an average diameter of approximately 18 mm (observed range 16.2-20.4 mm).

Unripe fruit is coloured near R.H.S.C.C. Yellow-Green 145 A.

The pedicel scar is very small, approximately 2.2 mm, similar to that of 'Centurion' and 'Centra Blue' fruit. The scar is generally dry.

Ripe fruit has an attractive intensity of bloom. Fruit colour is light blue with the bloom intact, near R.H.S.C.C. Blue group 102 D, and blue black (near R.H.S.C.C. Blue group 103 A) with the bloom removed similar to 'Maru'.

Sepals are erect to semi-erect in attitude, and are incurving as observed in the variety 'Delite' (not patented). The diameter of the calyx basin is medium, similar to that observed in the variety 'Powderblue' (not patented), while the calyx basin is shallow in depth.

The fruit sweetness (Brix level) averaged 12.8% (observed range 12.7-13.1 Brix). Overall, flavour has been observed to be balanced between sweetness and acidity.

Fruit is generally firm, similar to 'Centurion' and 'Maru'.

Yield is high, averaging approximately 8 Kg (observed range 6-12 Kg) per plant, this was observed to be higher than that of 'Maru' and 'Rahi' plants of similar age under New Zealand growing conditions. The self-compatibility of the new variety has not been tested by self-crossing the variety. However, it is recommended to associate the plant with other varieties with similar flowering timing to maximise pollination and fruit set.

Events

Vegetative bud burst occurred around 21$^{st}$ August under New Zealand growing conditions.

Time of beginning flowering was around 30$^{th}$ August, with the 50% of flowering around the 18$^{th}$ of September. This was slightly earlier than both 'Maru' (50% flowering occurring around 21$^{st}$ September) and 'Centurion' (50% flowering occurring around 25$^{th}$ September).

Maturity period: medium to late; fruit commenced ripening on trial plants at Ruakura, Hamilton, New Zealand in the first week of February reaching the 50% of blue fruit on the plant around the 15$^{th}$ of February. The time of fruit ripening occurs 2 weeks after that in New Zealand for 'Maru' (not patented) and one week to ten days after 'Centurion' (not patented).

Pest and Disease

The plant does not seem to be susceptible to rust (*Pucciniastrum vaccinii*). No symptoms of anthracnose or *Botryosphaeria* have been observed under New Zealand growing conditions.

Additional Description

The main harvest period is generally medium to late compared with other rabbiteye varieties and it is of long duration under the New Zealand growing conditions. The variety has been observed to be suited to production of blueberries for fresh consumption.

The plant cold hardiness according to the American zone classification has not been determined. However, the chilling requirement of 'Velluto Blue' has been estimated to be between 500-700 hours.

The invention claimed is:

1. A new and distinct blueberry plant substantially as illustrated and described.

* * * * *